(12) United States Patent
Merchak (10) Patent No.: US 7,839,501 B2
(45) Date of Patent: Nov. 23, 2010

(54) METHOD, APPARATUS AND SYSTEM FOR MEASURING THE TRANSPARENCY OF FILM

(75) Inventor: Paul Merchak, Loveland, OH (US)

(73) Assignee: Sun Chemical Corporation, Parsippany, NJ (US)

( * ) Notice: Subject to any disclaimer, the term of this patent is extended or adjusted under 35 U.S.C. 154(b) by 309 days.

(21) Appl. No.: 11/885,710

(22) PCT Filed: Mar. 2, 2006

(86) PCT No.: PCT/US2006/007629
§ 371 (c)(1),
(2), (4) Date: Jun. 9, 2008

(87) PCT Pub. No.: WO2006/096521

PCT Pub. Date: Sep. 14, 2006

(65) Prior Publication Data

US 2008/0278723 A1    Nov. 13, 2008

Related U.S. Application Data

(60) Provisional application No. 60/658,892, filed on Mar. 4, 2005.

(51) Int. Cl.
*G01J 3/42* (2006.01)

(52) U.S. Cl. .................................. 356/319

(58) Field of Classification Search ................. 356/319, 356/326, 328
See application file for complete search history.

(56) References Cited

U.S. PATENT DOCUMENTS

| 4,687,338 A | 8/1987 | Task et al. |
| 5,755,905 A * | 5/1998 | Sinn et al. .................... 156/184 |
| 5,920,831 A | 7/1999 | Pringle et al. |
| 6,139,618 A | 10/2000 | Hayashi et al. |
| 6,852,789 B2 | 2/2005 | Ochiai et al. |
| 2006/0008596 A1 | 1/2006 | Pokorny et al. |

FOREIGN PATENT DOCUMENTS

WO    WO2004076992 A2    9/2004

OTHER PUBLICATIONS

Fred W. Billmeyer, Jr., Yuan Chen, "On the Measurement of Haze," Color Research and Application, vol. 10, No. 4, Dec. 31, 1985, pp. 219-224, XP-002574379.
Supplementary European Search Report, Application No. EP 06 73 6879, Dated Mar. 25, 2010.

* cited by examiner

*Primary Examiner*—F. L Evans
(74) *Attorney, Agent, or Firm*—Kramer Levin Naftalis & Frankel LLP

(57) ABSTRACT

A method is disclosed for measuring four factors contributing to transparency of a colored film, namely, Haze, Scatter, Gloss and Bronze values by utilizing a diffuse sphere spectrophotometer.

28 Claims, 6 Drawing Sheets
(6 of 6 Drawing Sheet(s) Filed in Color)

METHOD, APPARATUS AND SYSTEM FOR MEASURING THE TRANSPARENCY OF FILM

CROSS REFERENCE TO RELATED APPLICATIONS

This application is the United States national stage filing of the corresponding international application number PCT/US2006/007629 filed on Mar. 2, 2006, which claims priority to and benefit of US provisional application no. 60/658,892 filed Mar. 4, 2005, each of which is hereby incorporated herein by reference.

FIELD OF THE INVENTION

The invention relates to a measurement method of four major contributing factors that lead to a reduction of transparency utilizing a diffuse sphere spectrophotometer. Specifically, the four factors are: Haze, Scatter, Gloss and Bronze.

BACKGROUND OF THE INVENTION

A perfectly transparent film when placed between an observer and an object does not reduce the clarity or contrast of the object. The addition of color to a film may or may not have a visible affect the clarity or contrast of an object depending on the interactions that the chromophor has with light and the saturation. The transparency may be reduced by significant absorption of light or other interactions of light with a film. These interactions may also lead to an observed angle dependence for transparency.

The difficulty with most measurement methods for transparency is that they attempt to use a single value to define transparency, while several factors actually contribute to transparency. Complicating factors such as haze, scatter, gloss and bronze combine to affect transparency and influence the degree and angle dependence of the observed and measured transparency. When a single value is used to describe transparency little or no knowledge is obtained on which physical-optical properties are contributing to the reduction in transparency or their relative contributions. The present invention provides a measurement method of four major contributing factors that lead to a reduction of transparency utilizing a diffuse sphere spectrophotometer. The four factors are: Haze, Scatter, Gloss and Bronze.

Methods have been developed to measure transparency and haze, by both transmission through a film and reflectance off of a film.

Methods for measuring transmission transparency and haze are known. The American Society for Testing and Materials (ASTM) D-1003, and the ISO 13468 standard test methods, provide measures that are non-compensated and compensated for the sphere efficiency, respectively, for Total Transmittance for transparency and Transmission Haze. These methods use collimated light projected through the object into an intergrated sphere. In U.S. Pat. No. 6,294,638, method ASTM D-1003 is utilized to measure the haze and total light transmittance using a Datacolor SF600 Plus-CT for transparent thermoplastic polyurethanes. In U.S. Pat. No. 6,660,793 the Hunter ColorQuest is used to provide transmission haze and transparency. BYK Gardner also supplies hazegard plus and haze-gard dual instruments for measuring transmission haze and total transmission.

Methods for measuring reflectance transparency and haze are also known. Systems have been developed to measure transparency and haze from one side of the material because films may be formed on opaque or translucent substrates or it may not be practical to position the test material between the light source and the detection system. H1,655 improves on U.S. Pat. Nos. 4,687,338 and 4,623,258 all to Task, et al by reducing directionality effects of the haze measurement by using a distributed annular light source for illuminating the transparent material. U.S. Pat. Nos. 5,451,253 and 6,706,863 teach the use of variation of the CIElab lightness, L*, to calculate the level of transparency. U.S. Pat. No. 6,706,863 teaches the conversion of the data to dL*, the difference between the L* for the conventional product and the samples, to show the degree of transparency. U.S. Pat. No. 5,451,253 teaches using of the dL* from a multi-angle spectrophotometer and measuring the difference in L* at 25° and 70° off of specular with an incident angle of 45° from normal. While both method provide a measure of transparency they do not provide a means for determining the source of the change in transparency.

ISO methods 2846 Part 1-4 describe methods for measuring transparency for printed inks using a 0/45 or 45/0 geometry spectrophotometer using the $\Delta E_{ab}$ color difference. The transparency measure is obtained by making multiple prints within a range of film thicknesses and measuring the $\Delta E_{ab}$ color difference relative to the black strip over which the ink was printed. The slope of the film thickness in microns plotted versus the $\Delta E_{ab}$ color difference provides the value for the transparency. The procedure states that negative slopes that are counterintuitive may be obtained. All of the methods that rely on a single value to define transparency have problems for consistently measuring highly transparent film with increasing or decreasing combinations of haze, scattering, gloss and bronze with varying film thickness or comparing a sample to a standard material. An example of this problem is a negative counterintuitive slope occurring in the ISO 2846 methods, that is easily explained using the present invention which separates the haze, scatter, gloss and bronze components of transparency.

Bronze effects have not been measured and have been misinterpreted. US (CIBA Bronze) describes a bronze pigment attributing the property to larger particle size. The bronze color observed in the patent is due to particle alignment not to particle size. Larger plate-like particles are more likely to align in the film providing the bronze effect evidenced by a bronze reflectance color observed for red pigments. It is the alignment of particles not the large particles that provide the bonze effect color. The bronze effect is readily apparent in a change in color that appears at the specular angle; for red pigments it appears as a bronzish color at specular, in blue and violet pigments it appears as a redish color at the specular angle. Bronze in a yellow film is described for the first time. Bronze in a yellow pigmented film provides a blue color at specular, but because blue & yellow are complementary colors this bronze is not visually observed as a color shift at specular but only as a higher gloss. Spectroscopically the bronze in a yellow film is readily observed when it is present.

SUMMARY OF THE INVENTION

The present invention provides a method for determining the Haze value of a film, comprising:
(a) determining the spectral response curve of said film using a specular excluded setting on a diffuse sphere spectrophotometer at a certain wavelength range; and
(b) determining said Haze value, wherein said Haze value is a member of the group consisting of:

(i) the spectral response at an individual wavelength along the baseline of said curve;
(ii) an average measure of all or part of said baseline; and
(iii) an integrated measure of all or part of said baseline.

The present invention also provides a method of determining the Scatter value of a film, comprising:
(a) determining the spectral response curve of said film using a specular excluded setting on a diffuse sphere spectrophotometer at a certain wavelength range; and
(b) determining said Scatter value, wherein said Scatter value is a member of the group consisting of:
(i) the spectral response at the peak of said curve minus the spectral response at the baseline of said curve;
(ii) width measure of all or part of said peak;
(iii) an average measure of the spectral response of all or part of said peak minus the spectral response at the baseline of said curve;
(iv) and an integrated spetral response measurement of all or part of said peak minus the integrated spectral response measurement at the baseline of said curve.

The present invention further provides a method of determining the Gloss value of a film, comprising:
(a) determining the spectral response curve of said film using a specular excluded setting on a diffuse sphere spectrophotometer at a certain wavelength range;
(b) determining the spectral response curve of said film using a specular included setting on a diffuse sphere spectrophotometer at a certain wavelength range; and
(c) determining said Gloss value, wherein said Gloss value is a member of the group consisting of:
(i) the difference between the spectral responses at any particular wavelength in the curve determined with a specular included setting and the curve determined with a specular excluded setting;
(ii) the difference between the average spectral responses at a range of wavelengths in the curve determined with a specular included setting and the curve determined with a specular excluded setting; and
(iii) the difference between the integrated spectral response at a range of wavelengths in the curve determined with a specular included setting and the curve determined with a specular excluded setting.

The present invention also provides a method of determining the Bronze value of a specific color of a film, comprising:
(a) determining the spectral response curve of said film using a specular included setting on a diffuse sphere spectrophotometer at a certain wavelength range; and
(b) determining said Bronze value, wherein said Bronze value is a member of the group consisting of:
(i) the spectral response at a shoulder of said curve minus the spectral response at the baseline of said curve wherein said shoulder is at a wavelength that is color specific;
(ii) an average measure of the spectral response of all or part of said shoulder minus the spectral response at the baseline of said curve; and
(iii) an integrated spectral response measurement of all or part of said shoulder minus the integrated spectral response measurement at the baseline of said curve.

The present invention further provides a method of determining the transparency of a film which is preferably on a black substrate and/or over a black background, said method comprising:
(a) determining the Haze, Scatter, Gloss and Bronze values of said film; and
(b) adding all or selected subset of the determined values in step (a) thereby determining the transparency of said film. One possible subset would include Haze, Scatter and Gloss. Bronze may not be included as it contributes to a portion of the Gloss.

The present invention also provides an apparatus capable of measuring the transparency of a film by determining the Haze, Scatter, Gloss and Bronze values.

Other objects and advantages of the present invention will become apparent from the following description and appended claims.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

This invention relates to a method for measuring factors contributing to transparency of a colored film, more particularly it describes the measurement of haze, scattering, gloss and pigment bronze utilizing a diffuse sphere spectrophotometer. In addition the method of the present invention provides values for these four factors from the same instrument.

The method of the present invention also provides a measurement system for haze, scatter, gloss and bronze on the same instrument and in the same measurement units of the spectral response, which is used to calculate coloristic properties for a colored film. The same factors in addition to other will combine to provide the spectral response when the film is printed over the white or natural background portion of the substrate.

When a film is applied on a black substrate the four factors haze, scatter, gloss and bronze, are the physical-optical properties that describe the interaction between the incident light and the film to provide the spectral responses. They uniquely contribute to different wavelength regions of the spectral response depending on instrument setting and the absorption band of the dyestuff. The two factors, haze and scatter, are observed in the non-specular spectral response and the other two factors, gloss and bronze, are observed in the specular reflectance spectral response.

The term film as described in the present invention may be an ink, paint or coating, or thermoplastic or thermoset plastic and may or may not be applied to a substrate. The substrate may be many types, including but not limited to, coated and uncoated paper, treated and untreated film, metal or ceramic surfaces. The measurements are made through the applied film with a black background. Films may be placed over a black background, but preferably a portion of the substrate is black. The film may be applied by many methods, but is not limited to, spraying, drawing down with a bar applicator, drawing down with a wire round rod applicator, an anilox roller, a flexographic, gravure or lithographic printing process, and extruding. The vehicle system may also be of a water-based, solvent-based, energy curable, 100% solid systems or combinations of these, but is not limited to these.

The non-specular spectral response is measured using the specular excluded instrument setting on the diffuse sphere spectrophotometer, while the non-specular and specular responses are combined in the specular included instrument setting on the diffuse sphere spectrophotometer.

Haze

Haze as described by the present invention results primarily from reflectance off of the rough film surface, though contributions to the haze measurement may come from within the film or back surface as well. The surface of the film is predominately comprised of the resins with refractive indices that are essentially independent of the wavelength of light within the visible wavelength region of the electromagnetic spectrum. This wavelength independent refractive index results in a haze that is independent of wavelength. Clear colorless films formed over a black substrate (e.g. for a clear overprint varnish) provide a near wavelength independent response measured at the specular excluded settings. The haze for colored films on a black substrate is measured in the absorption band of the dyestuff where minimum scattering occurs for the pigment. The magnitude of the minimum value in the spectral response correlates with the visual haze. The haze by the present invention is not limited to this measure of haze as there are other values which are expect to and do correlate with the minimum. Within the scope of the present invention the haze may alternatively be measured from a single wavelength on the baseline, an averaging of wavelengths of the baseline or by an integration of all or a portion of the area below the baseline. Preferably, the haze is measured at a wavelength range from about 400 to about 700 nm.

Scatter

Scatter as described by the present invention results from light scattering off of the colored dyestuff. The dyestuff is a colored particle, a pigment or an insoluble dye in the application media. Maximum scattering occurs on the low energy, high wavelength side of the absorption bands, the region of highest refractive index for the dyestuff. The scatter is a measure of the peak or maximum in the spectral response using the specular excluded setting for the diffuse sphere spectrophotometer. The measurement may or may not remove the haze background from the value. Preferably the haze level is removed from the scatter level. Preferably the scatter is the measure of the difference between the magnitude of the maximum in the spectral response and the magnitude of the haze as measured by the minimum value. Within the scope of the present invention the scatter may alternatively be measured from a single wavelength with the peak, an averaging of responses within the peak, an integration of all or a portion of the area below the peak or a measure of the peak breadth, all of which may or may not have haze contribution removed. Scatter is measured between 475 and 550 nm for a yellow, between 525 and 575 nm for an orange, between 550 and 650 nm for a red, less than 500 nm for a blue, between 450 and 580 nm for a green, and less than 500 nm or greater than 600 nm for a violet film.

Gloss

The specular included setting for the diffuse sphere spectrophotometer combines the non-specular, haze and scatter components, with the specular, gloss and bronze components. Gloss as described by the present invention results from the total specular reflectance contribution from the film while the bronze describes a specular reflectance contribution from the pigment particles.

Gloss as described by the present invention results from specular reflectance from the film. Typically the major contribution of the specular reflectance is from reflectance off of the film surface and is explained by geometric optics using Fresnel's Equation. The gloss component resulting from reflectance off of the resin with a near wavelength independent refractive index, will be almost independent of wavelength, while the gloss component resulting from reflectance off of the pigment with a wavelength dependent refractive index, will be wavelength dependent if the particles are oriented. Preferably, the gloss is measure by calculating the average increase of the specular included response over the specular excluded response (often at 10 nm interval) in the visible spectrum.

The gloss measure of the present invention is not limited to this measure as there are other values which are expect to and do correlate with the average value. Within the scope of the present invention the gloss may be from a single or the average of a few wavelengths by an integration of all or a portion of the area between the specular included and specular excluded responses.

Bronze

Bronze as described by the present invention results from specular reflectance off of oriented pigment at the pigment surface or within the film. The specular reflectance results from the difference in the refractive index between either the air or resin and the pigment. Like scatter the maximum bronze occurs in the low energy, high wavelength side and region of the absorption bands, the region of highest refractive index for the dyestuff. The bronze manifests itself in a shoulder or plateau on the high wavelength side of the absorption band. Preferably, the magnitude of the bronze is taken by measuring the height of the shoulder or plateau. The bronze as described by the present invention is a subset of the gloss component. The Bronze is preferably obtained by measuring the shoulder or plateau in a wavelength range that is color specific by the magnitude at an individual wavelength. Within the scope of the present invention the bronze may also be an average or integrated measure used to represent all or part of the shoulder or plateau, such as an average or integrated value. Bronze is measured between 400 and 550 nm for a yellow, between 450 and 600 nm for an orange, between 500 and 650 nm for a red, and between 550 and 700 nm for a green, blue or violet films.

Figure 1:
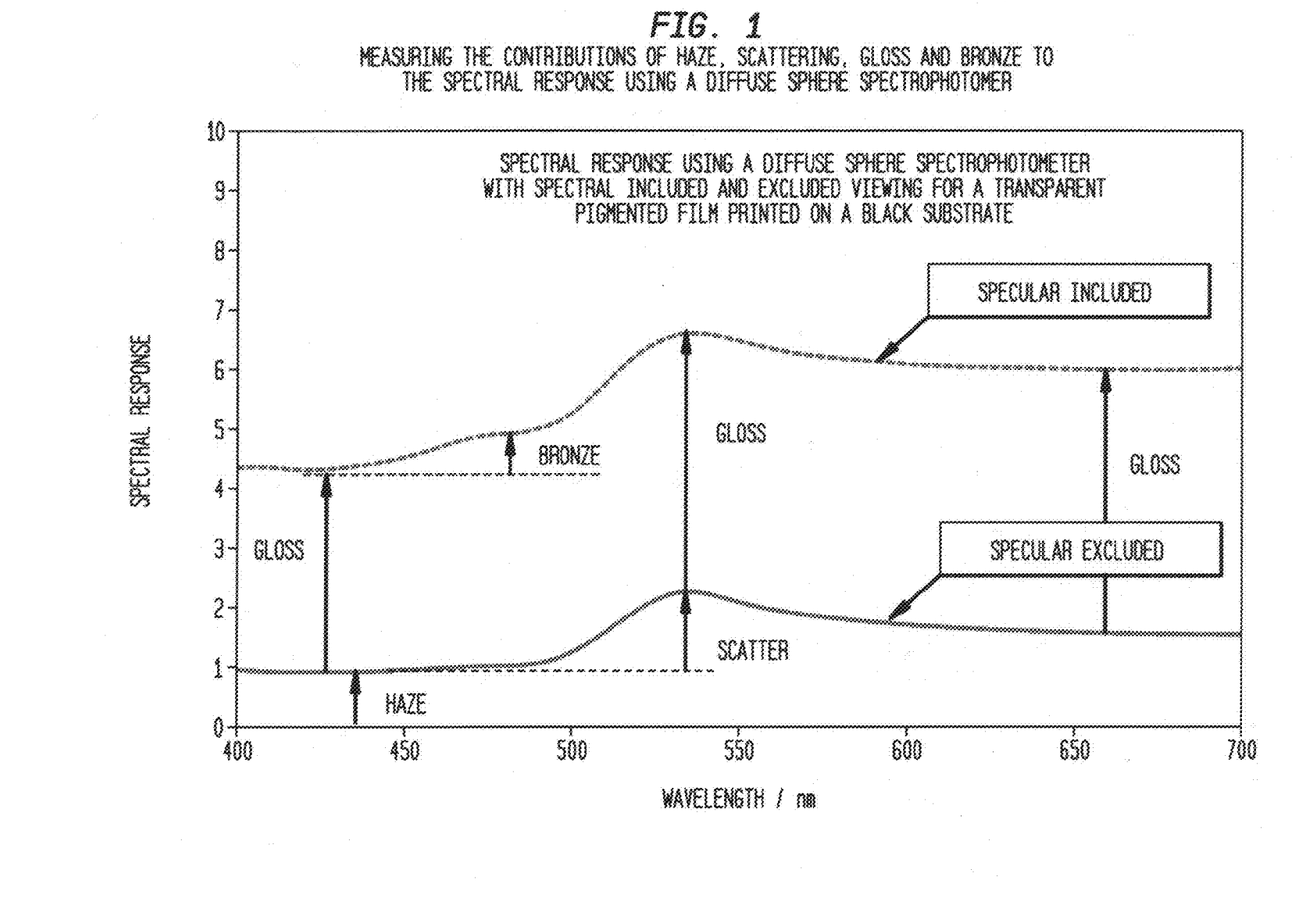
FIG. 1 shows a spectral response using a diffuse sphere spectrophotometer with specular included and excluded viewing for a transparent pigment film printed on a black substrate.

An example of the method described by the present invention to measure the relative magnitude of haze, scatter, gloss and bronze utilizing a diffuse sphere spectrophotometer for a yellow pigmented film is shown in FIG. 1.

The present method provides great flexibility and the ability to provide the haze, scatter, gloss and bronze efforts as absolute or relative numbers. Various methods of data manipulation and comparison are presented below, but the scope of the present invention should not be limited by them. Direct comparisons may be made where accurate targeted coating weights or film thicknesses are produced. When accurate coating weights or film thicknesses are produced but they are difficult to target, comparisons may be made through the use of linear regression to provide a value from a fitted model at a specific coating weight or film thickness. Direct comparisons may also be made when two samples are applied side-by-side on the same substrate at equal coating weight. Relative scales my also be derived by other mathematical manipulations such as subtracting, dividing or otherwise normalizing the values relative to some measured or theoretical standard.

EXAMPLE 1

Comparison of Three Transparent Yellow Pigmented Films

Figure 2:
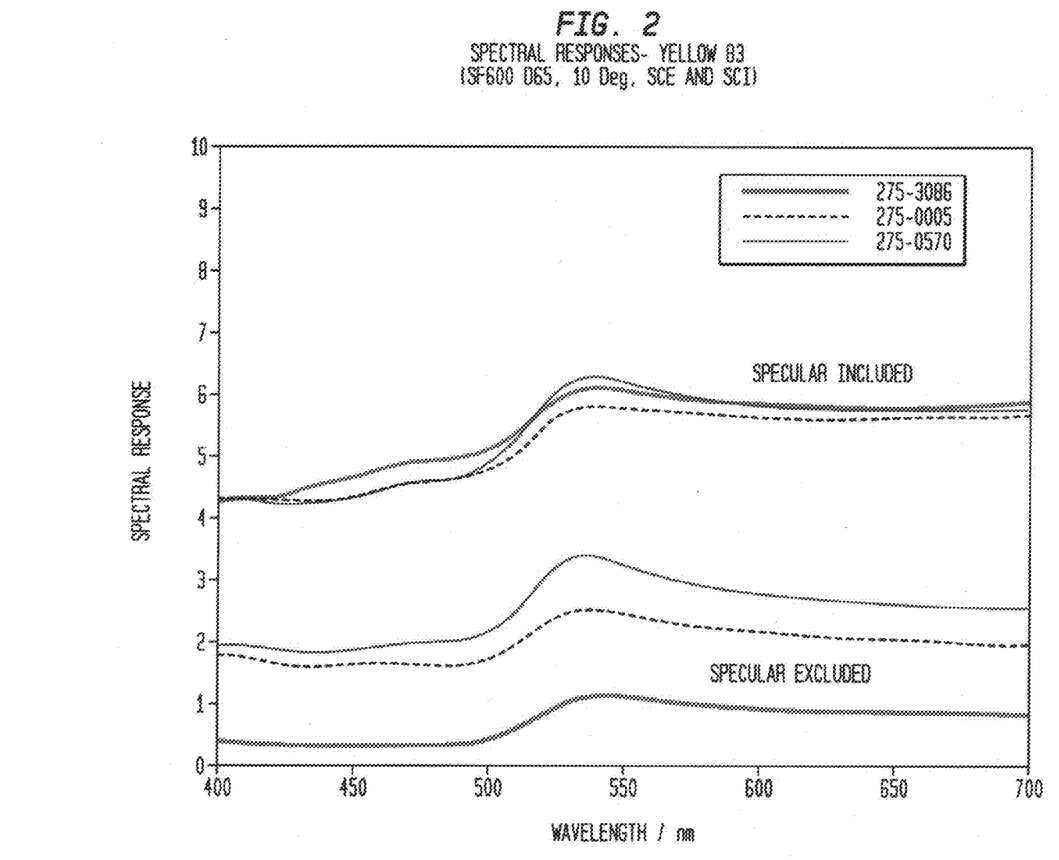
FIG. 2 shows the spectral responses with specular included and excluded viewing for three C.I. Pigment Yellow 83 based inks: 275-0005, 275-3086 and 275-0570.

Three nitrocellulose packaging gravure inks were evaluated on a Form 2A—Opacity stock from The Leneta Company. The inks were prepared from three C.I. Pigment Yellow 83 pigments, 275-0005, 275-3086 & 275-0570, from Sun Chemical Corporation. The spectral excluded and spectral included responses are measured on a Datacolor Spectraflash and the Haze, Scatter, Gloss and Bronze values determined. The spectral included and spectral excluded responses of the three yellow 83 pigments are plotted in FIG. 2 and shown in Tables 1 and 2 below.

TABLE 1

The Specular Excluded Spectral Response for three C.I. Yellow 83 Pigment inks: 275-0005, 275-3086 and 275-0570.

| Wavelength | 275-3086 | 275-0005 | 275-0570 |
|---|---|---|---|
| 400 | 0.42 | 1.8 | 1.95 |
| 410 | 0.4 | 1.74 | 1.96 |
| 420 | 0.38 | 1.66 | 1.88 |
| 430 | 0.37 | 1.6 | 1.86 |
| 440 | 0.36 | 1.6 | 1.86 |
| 450 | 0.36 | 1.61 | 1.88 |
| 460 | 0.36 | 1.61 | 1.92 |
| 470 | 0.37 | 1.62 | 1.99 |
| 480 | 0.36 | 1.62 | 2 |
| 490 | 0.38 | 1.63 | 2.03 |
| 500 | 0.46 | 1.71 | 2.18 |
| 510 | 0.64 | 1.96 | 2.53 |
| 520 | 0.89 | 2.28 | 3.02 |
| 530 | 1.09 | 2.47 | 3.33 |
| 540 | 1.14 | 2.49 | 3.35 |
| 550 | 1.13 | 2.43 | 3.24 |
| 560 | 1.08 | 2.35 | 3.11 |
| 570 | 1.04 | 2.29 | 2.99 |
| 580 | 1 | 2.25 | 2.9 |
| 590 | 0.98 | 2.2 | 2.84 |
| 600 | 0.94 | 2.16 | 2.78 |
| 610 | 0.93 | 2.13 | 2.73 |
| 620 | 0.92 | 2.09 | 2.69 |
| 630 | 0.9 | 2.06 | 2.67 |
| 640 | 0.88 | 2.04 | 2.64 |
| 650 | 0.88 | 2.03 | 2.62 |
| 660 | 0.89 | 2.01 | 2.6 |
| 670 | 0.89 | 1.99 | 2.59 |
| 680 | 0.88 | 1.97 | 2.56 |
| 690 | 0.87 | 1.95 | 2.55 |
| 700 | 0.87 | 1.95 | 2.55 |

TABLE 2

The Specular Included Spectral Response for three C.I. Yellow 83 Pigment inks: 275-0005, 275-3086 and 275-0570. Specular Included Spectral Response

| Wavelength | 275-3086 | 275-0005 | 275-0570 |
|---|---|---|---|
| 400 | 4.31 | 4.31 | 4.26 |
| 410 | 4.35 | 4.3 | 4.29 |
| 420 | 4.35 | 4.27 | 4.24 |
| 430 | 4.46 | 4.28 | 4.23 |
| 440 | 4.57 | 4.32 | 4.28 |
| 450 | 4.66 | 4.35 | 4.34 |
| 460 | 4.79 | 4.45 | 4.46 |
| 470 | 4.91 | 4.53 | 4.58 |
| 480 | 4.94 | 4.56 | 4.61 |
| 490 | 4.99 | 4.6 | 4.67 |
| 500 | 5.14 | 4.76 | 4.89 |
| 510 | 5.41 | 5.07 | 5.32 |
| 520 | 5.76 | 5.46 | 5.86 |
| 530 | 6.01 | 5.73 | 6.24 |
| 540 | 6.08 | 5.79 | 6.29 |
| 550 | 6.06 | 5.76 | 6.2 |
| 560 | 6.02 | 5.72 | 6.08 |
| 570 | 5.97 | 5.69 | 5.99 |
| 580 | 5.92 | 5.66 | 5.92 |
| 590 | 5.88 | 5.64 | 5.86 |
| 600 | 5.85 | 5.61 | 5.83 |
| 610 | 5.83 | 5.61 | 5.79 |
| 620 | 5.83 | 5.61 | 5.78 |
| 630 | 5.83 | 5.61 | 5.76 |
| 640 | 5.83 | 5.61 | 5.76 |
| 650 | 5.84 | 5.61 | 5.75 |
| 660 | 5.84 | 5.63 | 5.75 |
| 670 | 5.85 | 5.63 | 5.75 |
| 680 | 5.86 | 5.63 | 5.75 |
| 690 | 5.86 | 5.64 | 5.75 |
| 700 | 5.88 | 5.66 | 5.77 |

The haze was measured at the minimum response for the specular excluded response at 440 nm for each film. The scatter was measured by subtracting the haze value from the peak maximum for the specular excluded response at 540 nm for each film. The gloss was measured by averaging the difference between the specular included and specular excluded responses from 400-700 nm. The bronze was measured by subtracting the minimum response from the plateau at 480 nm for each of the three film specular included responses: 275-3086 (480-400 nm), 275-0005 (480-420 nm) and 275-0570 (480-430 nm.) The values are provided in the Table 3, with Tsum being the sum of the Haze, Scatter, Gloss and Bronze. The comparative value Y is also provided. This shows the correlation between the Tsum and the Y value, (as determined by the CIE 1976, known CIELAB system) but the Tsum is obtained from the four component parts.

TABLE 3

Values for Haze, Scatter, Gloss and Bronze for the three C.I. Yellow pigment inks along with Tsum and comparative Y value.

| | 275-3086 | 275-0005 | 275-0570 |
|---|---|---|---|
| Haze | 0.36 | 1.60 | 1.86 |
| Scatter | 0.78 | 0.89 | 1.49 |
| Gloss | 4.70 | 3.22 | 2.85 |
| Bronze | 0.63 | 0.29 | 0.38 |
| Tsum | 6.47 | 6.00 | 6.58 |
| Y | 5.76 | 5.47 | 5.76 |

EXAMPLE 2

Comparison of Transparent and Semi-Opaque Blue Pigmented Films

Figure 3:
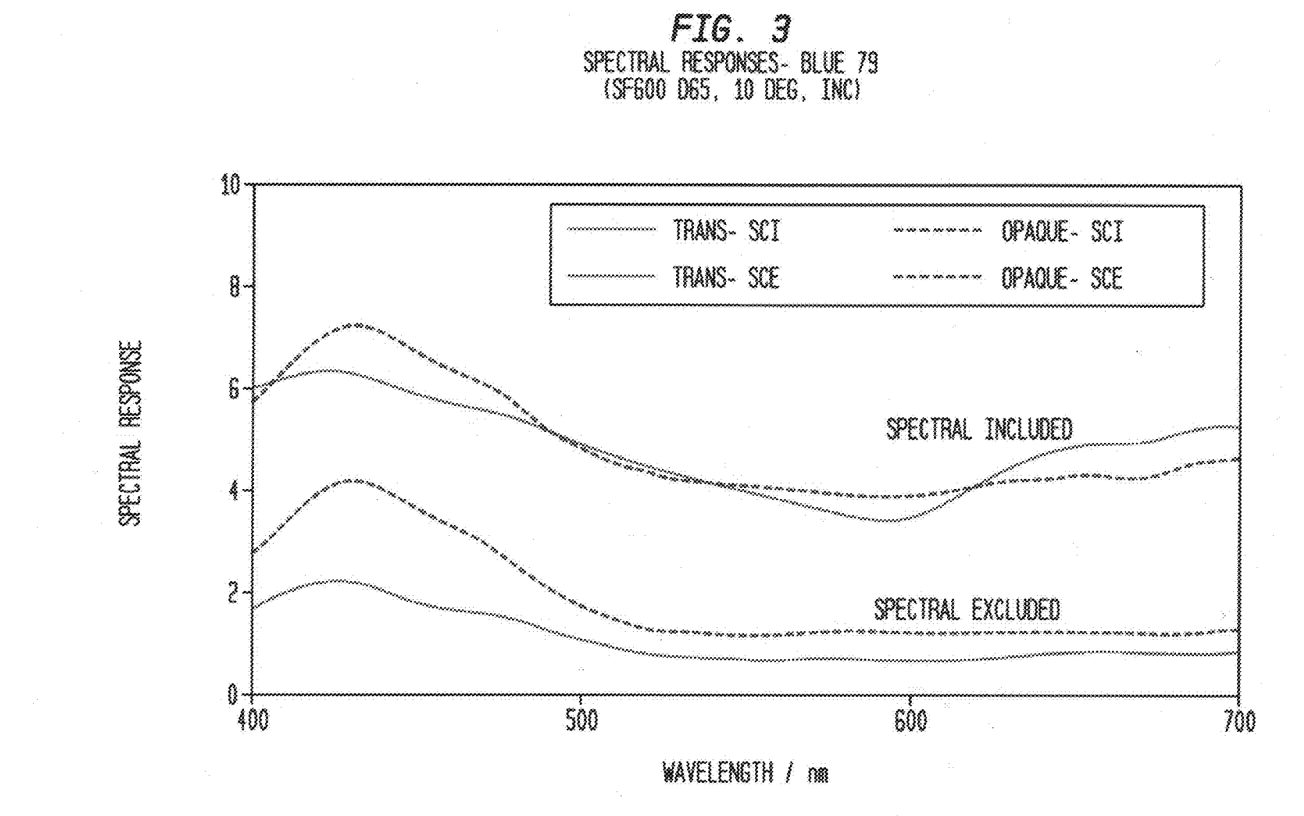
FIG. 3 shows the spectral responses with specular included and excluded viewing for a transparent and a semi-opaque version of C.I. Pigment Blue 79 ink.

Two water based flexo inks were evaluated on a Form 9A—Opacity Display stock from The Leneta Company. The inks were prepared from a transparent and a semi-opaque version of C.I. Pigment Blue 79. The spectral excluded and spectral included responses were measured on a Datacolor Spectraflash SF600 and the Haze, Scatter, Gloss and Bronze values determined. The spectral included and spectral excluded responses of the three yellow 83 pigments are plotted in FIG. 3 and shown in Table 4 below.

TABLE 4

The Specular Included and Specular Excluded Spectral Response for the transparent and the semi-opaque version of C.I. Pigment Blue 79 inks.

| Wavelength | Trans - SCI | Semi-Opaque - SCI | Trans - SCE | Semi-Opaque - SCE |
|---|---|---|---|---|
| 400 | 5.96 | 5.72 | 1.62 | 2.71 |
| 410 | 6.19 | 6.33 | 1.95 | 3.29 |
| 420 | 6.3 | 6.92 | 2.14 | 3.89 |
| 430 | 6.24 | 7.14 | 2.14 | 4.11 |
| 440 | 6.07 | 7.02 | 1.95 | 3.91 |
| 450 | 5.83 | 6.64 | 1.75 | 3.54 |
| 460 | 5.65 | 6.32 | 1.61 | 3.23 |
| 470 | 5.53 | 6.03 | 1.51 | 2.89 |
| 480 | 5.36 | 5.61 | 1.38 | 2.45 |
| 490 | 5.13 | 5.16 | 1.19 | 2.01 |
| 500 | 4.88 | 4.8 | 1.04 | 1.66 |
| 510 | 4.65 | 4.5 | 0.89 | 1.4 |
| 520 | 4.43 | 4.3 | 0.77 | 1.22 |
| 530 | 4.25 | 4.18 | 0.71 | 1.15 |
| 540 | 4.09 | 4.09 | 0.66 | 1.12 |
| 550 | 3.94 | 4.04 | 0.64 | 1.13 |
| 560 | 3.8 | 3.98 | 0.63 | 1.14 |
| 570 | 3.65 | 3.93 | 0.64 | 1.15 |
| 580 | 3.5 | 3.87 | 0.63 | 1.15 |
| 590 | 3.38 | 3.86 | 0.61 | 1.15 |
| 600 | 3.43 | 3.88 | 0.61 | 1.15 |
| 610 | 3.69 | 3.93 | 0.63 | 1.14 |
| 620 | 4.05 | 4.01 | 0.67 | 1.15 |
| 630 | 4.4 | 4.09 | 0.72 | 1.16 |
| 640 | 4.67 | 4.16 | 0.76 | 1.17 |
| 650 | 4.83 | 4.21 | 0.77 | 1.17 |
| 660 | 4.91 | 4.23 | 0.79 | 1.17 |
| 670 | 4.92 | 4.22 | 0.77 | 1.13 |
| 680 | 5.04 | 4.34 | 0.76 | 1.14 |
| 690 | 5.18 | 4.5 | 0.76 | 1.18 |
| 700 | 5.25 | 4.59 | 0.79 | 1.23 |

The haze is measured at the minimum response for the specular excluded response at 590 and 540 nm for the transparent and semi-opaque product, respectively. The scatter is measured by subtracting the haze value from the peak maximum for the specular excluded response at 430 nm for each film. The gloss is measured by averaging the difference between the specular included and specular excluded responses from 400-700 nm. The bronze is measured by subtracting the minimum response at 590 nm from the plateau at 660 nm for each film. The values are provided in the Table 5 with Tsum being the sum of the Haze, Scatter, Gloss and Bronze. The comparative value Y is also provided.

TABLE 5

Values for Haze, Scatter, Gloss and Bronze for the transparent and the semi-opaque version of C.I. Pigment Blue 79 inks along with Tsum and comparative Y value.

|  | Transparent | Semi-Opaque |
|---|---|---|
| Haze | 0.61 | 1.12 |
| Scatter | 1.53 | 2.99 |
| Bronze | 1.53 | 0.37 |
| Gloss | 3.76 | 3.02 |
| Tsum | 7.43 | 7.50 |
| Y | 4.16 | 4.28 |

EXAMPLE 3

Comparison of Three Yellow Films of Varying Transparency

Figure 4:
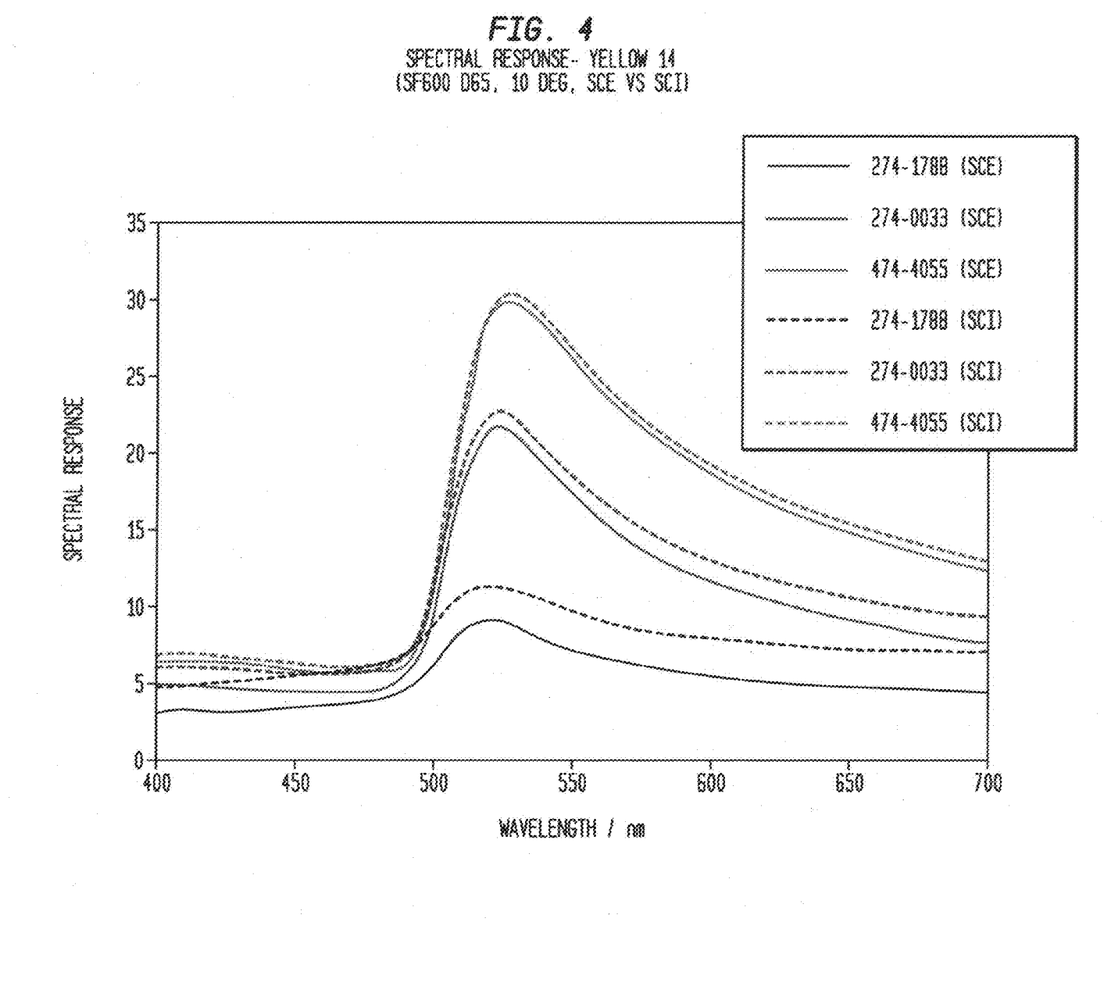
FIG. 4 shows the spectral responses with specular included and excluded viewing for the three C.I. Pigment Yellow 14 based inks from Sun Chemical Corporation; 274-1788, 274-0033 and 474-4055.

Three water based flexo inks were evaluated on a Form 2A—Opacity stock from The Leneta Company. The inks were prepared from three samples of C.I. Pigment Yellow 14 from Sun Chemical Corporation; 274-1788, 274-0033 & 474-4055. The spectral excluded and spectral included responses were measured on a Datacolor Spectraflash SF600 and the Haze, Scatter, Gloss and Bronze values determined. The spectral included and spectral excluded responses of the three C.I. Pigment Yellow 14 are plotted in FIG. 4 and shown in Table 6 below.

TABLE 6

The Specular Included and Specular Excluded Spectral Response for the three C.I. Pigment Yellow 14 inks from Sun Chemical Corporation; 274-1788, 274-0033 and 474-4055.

| Wavelength | 274-1788 (SCE) | 274-0033 (SCE) | 474-4055 (SCE) | 274-1788 (SCI) | 274-0033 (SCI) | 474-4055 (SCI) |
|---|---|---|---|---|---|---|
| 400 | 3.08 | 5.03 | 6.35 | 4.61 | 5.87 | 6.68 |
| 410 | 3.12 | 4.95 | 6.37 | 4.73 | 5.87 | 6.7 |
| 420 | 3.08 | 4.77 | 6.19 | 4.81 | 5.73 | 6.53 |
| 430 | 3.15 | 4.67 | 6.06 | 4.98 | 5.67 | 6.43 |
| 440 | 3.3 | 4.64 | 6.01 | 5.21 | 5.6 | 6.36 |
| 450 | 3.4 | 4.51 | 5.77 | 5.4 | 5.5 | 6.13 |
| 460 | 3.45 | 4.39 | 5.55 | 5.51 | 5.41 | 5.94 |
| 470 | 3.54 | 4.4 | 5.59 | 5.68 | 5.47 | 6 |
| 480 | 3.86 | 4.63 | 5.75 | 6.09 | 5.73 | 6.14 |
| 490 | 4.54 | 5.6 | 6.38 | 6.84 | 6.72 | 6.79 |
| 500 | 6.2 | 9.95 | 11.01 | 8.5 | 11.07 | 11.41 |
| 510 | 8.3 | 17.74 | 21.99 | 10.57 | 18.78 | 22.36 |
| 520 | 8.97 | 21.56 | 29.3 | 11.22 | 22.55 | 29.66 |
| 530 | 8.51 | 20.95 | 29.87 | 10.77 | 21.96 | 30.22 |
| 540 | 7.8 | 19.09 | 28.14 | 10.05 | 20.12 | 28.48 |
| 550 | 7.16 | 17.25 | 26.02 | 9.43 | 18.34 | 26.39 |
| 560 | 6.64 | 15.7 | 24.11 | 8.92 | 16.82 | 24.48 |
| 570 | 6.21 | 14.4 | 22.47 | 8.52 | 15.58 | 22.86 |
| 580 | 5.89 | 13.32 | 21.03 | 8.19 | 14.53 | 21.44 |
| 590 | 5.62 | 12.4 | 19.78 | 7.93 | 13.65 | 20.19 |
| 600 | 5.39 | 11.63 | 18.69 | 7.71 | 12.92 | 19.11 |
| 610 | 5.21 | 10.96 | 17.7 | 7.54 | 12.29 | 18.13 |
| 620 | 5.04 | 10.37 | 16.81 | 7.39 | 11.74 | 17.28 |
| 630 | 4.91 | 9.86 | 16.04 | 7.27 | 11.27 | 16.52 |
| 640 | 4.79 | 9.41 | 15.35 | 7.18 | 10.86 | 15.84 |
| 650 | 4.69 | 9.03 | 14.73 | 7.1 | 10.51 | 15.23 |
| 660 | 4.62 | 8.68 | 14.19 | 7.03 | 10.19 | 14.7 |
| 670 | 4.54 | 8.36 | 13.65 | 6.97 | 9.9 | 14.18 |
| 680 | 4.46 | 8.04 | 13.15 | 6.91 | 9.64 | 13.7 |
| 690 | 4.4 | 7.77 | 12.71 | 6.85 | 9.4 | 13.27 |
| 700 | 4.36 | 7.56 | 12.33 | 6.83 | 9.23 | 12.93 |

The haze is measured at the minimum response for the specular excluded response at 400 nm for 274-1788, and at 460 nm for both 274-0033 and 474-4055. The scatter is measured by subtracting the haze value from the peak maximum for the specular excluded response at 520 nm for both 274-1788 and 274-0033, and at 530 nm for 474-4055. The gloss is measured by averaging the difference between the specular included and specular excluded responses from 400-700 nm. The bronze is measured by subtracting the minimum response at 400 nm from the plateau at 470 nm for the specular included response for only 274-1788, 274-0033 and 474-4055 exhibited no plateau. The values are provided in the Table 7 with Tsum being the sum of the Haze, Scatter, Gloss and Bronze. The comparative value Y is also provided.

TABLE 7

Values for Haze, Scatter, Gloss and Bronze for the three C.I. Pigment Yellow 14 inks from Sun Chemical Corporation; 274-1788, 274-0033 and 474-4055 along with Tsum and comparative Y value.

|  | 274-1788 | 274-0033 | 474-4055 |
|---|---|---|---|
| Haze | 3.08 | 4.39 | 5.55 |
| Scatter | 5.89 | 17.17 | 24.32 |
| Bronze | 1.48 | 0 | 0 |
| Gloss | 2.21 | 1.20 | 0.42 |
| Tsum | 12.66 | 22.76 | 30.29 |
| Y | 8.73 | 15.43 | 21.36 |

EXAMPLE 4

Comparison of Two Blue Films in UV Cured Ink

Figure 5:
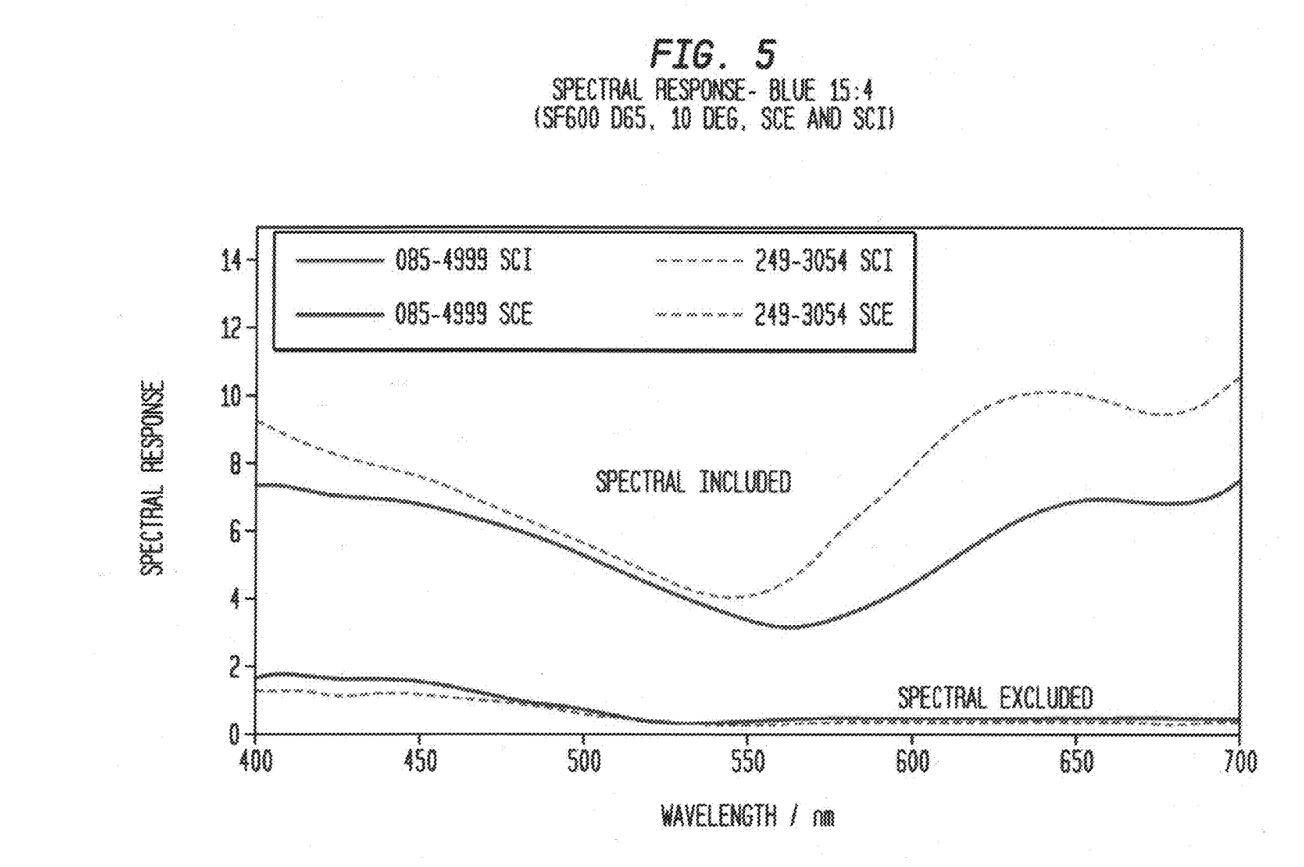
FIG. 5 shows the spectral responses with specular included and excluded viewing for the two transparent C.I. Pigment Blue 15:4 inks: 085-4999 and 249-3054.

Two UV cured flexo inks were evaluated on a Form 9A—Opacity Display stock from The Leneta Company. The inks were prepared from two transparent C.I. Pigment Blue 15:4 pigments: 085-4999 and 249-3054. The spectral excluded and spectral included responses were measured on a Datacolor Spectraflash SF600 and the Haze, Scatter, Gloss and Bronze values determined. The spectral included and spectral excluded responses of the two transparent C.I. Pigment Blue 15:4 pigments are plotted in FIG. 5 and shown in Table 8 below.

TABLE 8

The Specular Included and Specular Excluded Spectral Response for the two transparent C.I. Pigment Blue 15:4 inks: 085-4999 and 249-3054.

|  | 085-4999 SCI | 249-3054 SCI | 085-4999 SCE | 249-3054 SCE |
|---|---|---|---|---|
| 400 | 7.32 | 9.26 | 1.6 | 1.18 |
| 410 | 7.26 | 8.8 | 1.69 | 1.15 |
| 420 | 7.07 | 8.36 | 1.58 | 1.08 |
| 430 | 6.93 | 8.04 | 1.53 | 1.05 |
| 440 | 6.94 | 7.87 | 1.57 | 1.07 |
| 450 | 6.82 | 7.57 | 1.5 | 1.04 |
| 460 | 6.53 | 7.18 | 1.29 | 0.94 |
| 470 | 6.23 | 6.82 | 1.13 | 0.86 |
| 480 | 5.94 | 6.45 | 0.97 | 0.77 |
| 490 | 5.61 | 6.05 | 0.81 | 0.67 |
| 500 | 5.25 | 5.63 | 0.64 | 0.55 |
| 510 | 4.85 | 5.16 | 0.48 | 0.41 |
| 520 | 4.41 | 4.68 | 0.36 | 0.31 |
| 530 | 4.01 | 4.28 | 0.28 | 0.21 |
| 540 | 3.65 | 4.02 | 0.27 | 0.17 |
| 550 | 3.31 | 4 | 0.31 | 0.21 |
| 560 | 3.12 | 4.37 | 0.35 | 0.24 |
| 570 | 3.2 | 5.17 | 0.38 | 0.26 |
| 580 | 3.54 | 6.14 | 0.4 | 0.26 |
| 590 | 3.92 | 6.99 | 0.4 | 0.26 |
| 600 | 4.39 | 7.88 | 0.4 | 0.26 |
| 610 | 5.03 | 8.83 | 0.41 | 0.26 |
| 620 | 5.64 | 9.49 | 0.41 | 0.27 |
| 630 | 6.17 | 9.86 | 0.42 | 0.27 |
| 640 | 6.61 | 10.07 | 0.42 | 0.26 |
| 650 | 6.86 | 10.02 | 0.4 | 0.26 |
| 660 | 6.88 | 9.76 | 0.39 | 0.26 |
| 670 | 6.77 | 9.49 | 0.38 | 0.24 |
| 680 | 6.78 | 9.53 | 0.38 | 0.23 |
| 690 | 6.97 | 9.84 | 0.38 | 0.24 |
| 700 | 7.5 | 10.6 | 0.4 | 0.25 |

The haze is measured at the minimum response for the specular excluded response at 540 nm. The scatter is measured by subtracting the haze value from the maximum of the specular excluded response at 400 nm for each film. The gloss is measured by averaging the difference between the specular included and specular excluded responses from 400-700 nm. The bronze is measured by subtracting the minimum response at 560 nm from the plateau at 660 nm for 085-499 and the minimum at 550 nm from the plateau at 640 nm for 249-3054. The values are provided in Table 9 with Tsum being the sum of the Haze, Scatter, Gloss and Bronze. The comparative value Y is also provided.

TABLE 9

Values for Haze, Scatter, Gloss and Bronze for the two transparent C.I. Pigment Blue 15:4 inks: 085-4999 and 249-3054 along with Tsum and comparative Y value.

|  | 085-4999 | 249-3054 |
|---|---|---|
| Haze | 0.27 | 0.17 |
| Scatter | 1.33 | 1.01 |
| Bronze | 3.76 | 6.07 |
| Gloss | 4.95 | 6.99 |
| Tsum | 10.31 | 14.24 |
| Y | 4.33 | 5.81 |

EXAMPLE 5

Comparison of Dispersion for Red Pigment

Figure 6:
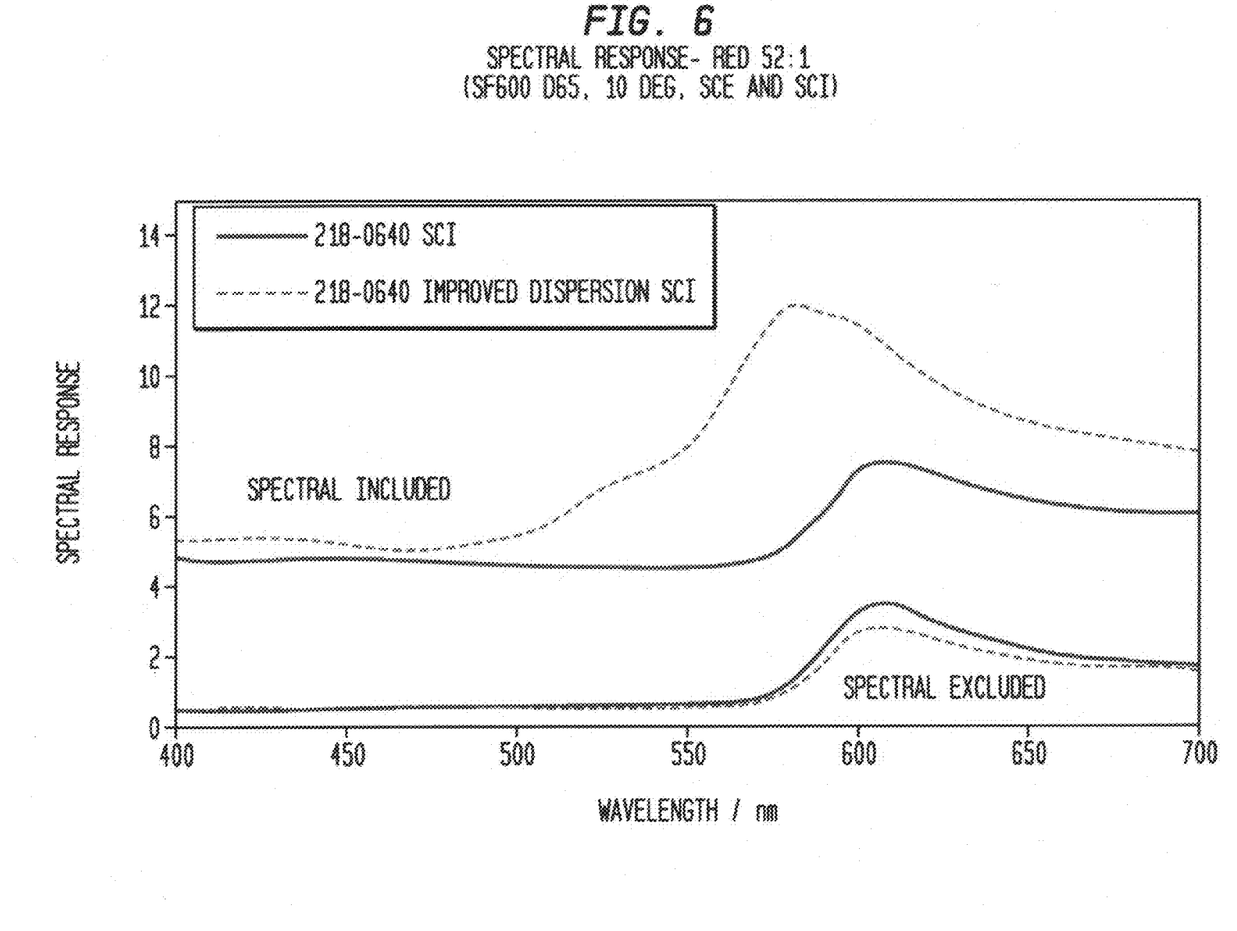
FIG. 6 shows the spectral responses with specular included and excluded viewing for the two C.I. Pigment Red 52:1 218-0640 inks.

Two UV cured flexo inks were evaluated on a Form 9A—Opacity Display stock from The Leneta Company. The inks were prepared from a transparent C.I. Pigment Red 52:1, 218-0640 from Sun Chemical Corporation. The spectral excluded and spectral included responses were measured on a Datacolor Spectraflash SF600 and the Haze, Scatter, Gloss and Bronze values determined. The spectral included and spectral excluded responses of the two C.I. Pigment Red 52:1 218-0640 inks are plotted in FIG. 6 and shown in Table 10 below.

TABLE 10

The Specular Included and Specular Excluded Spectral Response for the two C.I. Pigment Red 52:1 218-0640 inks.

|     | 218-0640 SCI | 218-0640 Improved Dispersion SCI | 218-0640 SCE | 218-0640 Improved Dispersion SCE |
| --- | --- | --- | --- | --- |
| 400 | 4.77 | 5.29  | 0.46 | 0.44 |
| 410 | 4.71 | 5.29  | 0.44 | 0.42 |
| 420 | 4.72 | 5.34  | 0.44 | 0.45 |
| 430 | 4.72 | 5.33  | 0.47 | 0.47 |
| 440 | 4.73 | 5.26  | 0.5  | 0.48 |
| 450 | 4.73 | 5.13  | 0.51 | 0.5  |
| 460 | 4.71 | 5.04  | 0.52 | 0.5  |
| 470 | 4.68 | 5     | 0.52 | 0.5  |
| 480 | 4.65 | 5.07  | 0.52 | 0.49 |
| 490 | 4.63 | 5.19  | 0.52 | 0.47 |
| 500 | 4.6  | 5.42  | 0.53 | 0.48 |
| 510 | 4.58 | 5.79  | 0.54 | 0.49 |
| 520 | 4.55 | 6.37  | 0.55 | 0.49 |
| 530 | 4.54 | 6.96  | 0.55 | 0.48 |
| 540 | 4.52 | 7.37  | 0.54 | 0.47 |
| 550 | 4.53 | 7.9   | 0.58 | 0.49 |
| 560 | 4.58 | 9.07  | 0.68 | 0.53 |
| 570 | 4.72 | 10.84 | 0.84 | 0.61 |
| 580 | 5.14 | 11.86 | 1.22 | 0.93 |
| 590 | 6.16 | 11.78 | 2.19 | 1.73 |
| 600 | 7.3  | 11.42 | 3.26 | 2.55 |
| 610 | 7.57 | 10.77 | 3.45 | 2.71 |
| 620 | 7.29 | 10.05 | 3.11 | 2.48 |
| 630 | 6.94 | 9.47  | 2.71 | 2.22 |
| 640 | 6.67 | 9.03  | 2.42 | 2.01 |
| 650 | 6.47 | 8.68  | 2.18 | 1.85 |
| 660 | 6.34 | 8.45  | 2.03 | 1.74 |
| 670 | 6.23 | 8.24  | 1.91 | 1.65 |
| 680 | 6.16 | 8.08  | 1.81 | 1.59 |
| 690 | 6.1  | 7.95  | 1.75 | 1.55 |
| 700 | 6.09 | 7.87  | 1.69 | 1.51 |

The haze is measured at the minimum response for the specular excluded response at 410 nm for both films. The scatter is measured by subtracting the haze value from the peak maximum for the specular excluded response at 610 nm for both. The gloss is measured by averaging the difference between the specular included and specular excluded responses from 400-700 nm. The bronze is measured by subtracting the minimum response at 470 nm from the shoulder at 540 nm for the specular included response for only the Improved Dispersion 218-0640. The 218-0640 control shows no bronze. The values are provided in Table 11 with Tsum being the sum of the Haze, Scatter, Gloss and Bronze. The comparative value Y is also provided.

TABLE 11

Values for Haze, Scatter, Gloss and Bronze for the two C.I. Pigment Red 52:1 218-0640 inks along with Tsum and comparative Y value.

|         | 218-0640 Control | Improved Dispersion 218-0640 |
| ---     | --- | --- |
| Haze    | 0.44 | 0.42 |
| Scatter | 3.41 | 2.29 |
| Bronze  | 0    | 2.37 |
| Gloss   | 4.15 | 6.52 |
| Tsum    | 8.0  | 11.6 |
| Y       | 5.17 | 8.41 |

The invention has been described in terms of preferred embodiments thereof, but is more broadly applicable as will be understood by those skilled in the art. The scope of the invention is only limited by the following claim

What is claimed is:

1. A method for determining the Haze value of a film, comprising:
    (a) determining the spectral response curve of said film using a specular excluded setting on a diffuse sphere spectrophotometer at a certain wavelength range; and
    (b) determining said Haze value, wherein said Haze value is a member of the group consisting of:
        (i) the spectral response at an individual wavelength along the baseline of said curve;
        (ii) an average measure of all or part of said baseline; and
        (iii) an integrated measure of all or part of said baseline.

2. The method of claim 1, wherein the determination of the spectral response curve in step (a) is carried out with the film being on a black substrate and/or over a black background.

3. The method of claim 1, wherein said wavelength range is from about 400 to about 700 nm.

4. The method of claim 1, wherein said Haze value is the spectral response at an individual wavelength along the baseline of said curve.

5. A method of determining the Scatter value of a film, comprising:
    (a) determining the spectral response curve of said film using a specular excluded setting on a diffuse sphere spectrophotometer at a certain wavelength range; and
    (b) determining said Scatter value, wherein said Scatter value is a member of the group consisting of:
        (i) the spectral response at the peak of said curve minus the spectral response at the baseline of said curve;
        (ii) width measure of all or part of said peak;
        (iii) an average measure of the spectral response of all or part of said peak minus the spectral response at the baseline of said curve; and
        (iv) an integrated spectral response measurement of all or part of said peak minus the integrated spectral response measurement at the baseline of said curve.

6. The method of claim 5, wherein the determination of the spectral response curve in step (a) is carried out with the film being on a black substrate and/or over a black background.

7. The method of claim 5, wherein said film is yellow and the peak of said curve is at a wavelength from about 500 to about 550 nm.

8. The method of claim 5, wherein said film is orange and the peak of said curve is at a wavelength from about 525 to about 575 nm.

9. The method of claim 5, wherein said film is red and the peak of said curve is at a wavelength from about 550 to about 650 nm.

10. The method of claim 5, wherein said film is blue and the peak of said curve is at a wavelength from about 420 to about 480 nm.

11. The method of claim 5, wherein said film is green and the peak of said curve is at a wavelength from about 450 to about 500 nm.

12. A method of determining the Gloss value of a film, comprising:
    (a) determining the spectral response curve of said film using a specular excluded setting on a diffuse sphere spectrophotometer at a certain wavelength range;
    (b) determining the spectral response curve of said film using a specular included setting on a diffuse sphere spectrophotometer at a certain wavelength range; and
    (c) determining said Gloss value, wherein said Gloss value is a member of the group consisting of:

(i) the difference between the spectral responses at any particular wavelength in the curve determined with a specular included setting and the curve determined with a specular excluded setting;

(ii) the difference between the average spectral responses at a range of wavelengths in the curve determined with a specular included setting and the curve determined with a specular excluded setting; and (iii) the difference between the integrated spectral response at a range of wavelengths in the curve determined with a specular included setting and the curve determined with a specular excluded setting.

13. The method of claim 12, wherein the determination of the spectral response curves in steps (a) and (b) is carried out with the film being on a black substrate and/or over a black background.

14. The method of claim 12, wherein said wavelength range is from about 400 to about 700 nm.

15. A method of determining the Bronze value of a specific color of a film, comprising:
   (a) determining the spectral response curve of said film using a specular included setting on a diffuse sphere spectrophotometer at a certain wavelength range; and
   (b) determining said Bronze value, wherein said Bronze value is a member of the group consisting of:
      (i) the spectral response at a shoulder of said curve minus the spectral response at the baseline of said curve wherein said shoulder is at a wavelength that is color specific;
      (ii) an average measure of the spectral response of all or part of said shoulder minus the spectral response at the baseline of said curve; and
      (iii) an integrated spectral response measurement of all or part of said shoulder minus the integrated spectral response measurement at the baseline of said curve.

16. The method of claim 15, wherein the determination of the spectral response curve in step (a) is carried out with the film being on a black substrate and/or over a black background.

17. The method of claim 15, wherein the color is yellow and the shoulder is measured at a wavelength from about 400 to about 550 nm.

18. The method of claim 15, wherein the color is orange and the shoulder is measured at a wavelength from about 450 to about 600 nm.

19. The method of claim 15, wherein the color is red and the shoulder is measured at a wavelength from about 500 to about 650 nm.

20. The method of claim 15, wherein the color is selected from the group consisting of green, blue and violet and the shoulder is measured at a wavelength from about 550 to about 700 nm.

21. A method of determining the transparency of a film comprising:
   (1) determining the Haze, Scatter, Gloss and Bronze values of said film; and
   (2) adding all or selected subset of the determined values in step (1) thereby determining the transparency of said film,
wherein said Haze value is determined by a method which comprises:
   (a) determining the spectral response curve of said film using a specular excluded setting on a diffuse sphere spectrophotometer at a certain wavelength range; and
   (b) determining said Haze value, wherein said Haze value is a member of the group consisting of:
      (i) the spectral response at an individual wavelength along the baseline of said curve;
      (ii) an average measure of all or part of said baseline; and
      (iii) an integrated measure of all or part of said baseline.

22. The method of claim 21, wherein the determination of the spectral response curve in step (a) is carried out with the film being on a black substrate and/or over a black background.

23. A method of determining the transparency of a film comprising:
   (1) determining the Haze, Scatter, Gloss and Bronze values of said film; and
   (2) adding all or selected subset of the determined values in step (1) thereby determining the transparency of said film,
wherein said Scatter value is determined by a method which comprises:
   (a) determining the spectral response curve of said film using a specular excluded setting on a diffuse sphere spectrophotometer at a certain wavelength range; and
   (b) determining said Scatter value, wherein said Scatter value is a member of the group consisting of:
      (i) the spectral response at the peak of said curve minus the spectral response at the baseline of said curve;
      (ii) width measure of all or part of said peak;
      (iii) an average measure of the spectral response of all or part of said peak minus the spectral response at the baseline of said curve;
      (iv) and an integrated spectral response measurement of all or part of said peak minus the integrated spectral response measurement at the baseline of said curve.

24. The method of claim 23, wherein the determination of the spectral response curve in step (a) is carried out with the film being on a black substrate and/or over a black background.

25. A method of determining the transparency of a film comprising:
   (1) determining the Haze, Scatter, Gloss and Bronze values of said film; and
   (2) adding all or selected subset of the determined values in step (1) thereby determining the transparency of said film,
wherein said Gloss value is determined by a method which comprises:
   (a) determining the spectral response curve of said film using a specular excluded setting on a diffuse sphere spectrophotometer at a certain wavelength range;
   (b) determining the spectral response curve of said film using a specular included setting on a diffuse sphere spectrophotometer at a certain wavelength range; and
   (c) determining said Gloss value, wherein said Gloss value is a member of the group consisting of:
      (i) the difference between the spectral responses at any particular wavelength in the curve determined with a specular included setting and the curve determined with a specular excluded setting;
      (ii) the difference between the average spectral responses at a range of wavelengths in the curve determined with a specular included setting and the curve determined with a specular excluded setting; and
      (iii) the difference between the integrated spectral response at a range of wavelengths in the curve determined with a specular included setting and the curve determined with a specular excluded setting.

26. The method of claim 25, wherein the determination of the spectral response curves in steps (a) and (b) is carried out with the film being on a black substrate and/or over a black background.

27. A method of determining the transparency of a film comprising:
   (1) determining the Haze, Scatter, Gloss and Bronze values of said film; and
   (2) adding all or selected subset of the determined values in step (1) thereby determining the transparency of said film, wherein said Bronze value is determined by a method which comprises:
   (a) determining the spectral response curve of said film using a specular included setting on a diffuse sphere spectrophotometer at a certain wavelength range; and
   (b) determining said Bronze value, wherein said Bronze value is a member of the group consisting of:
      (i) the spectral response at a shoulder of said curve minus the spectral response at the baseline of said curve wherein said shoulder is at a wavelength that is color specific;
      (ii) an average measure of the spectral response of all or part of said shoulder minus the spectral response at the baseline of said curve; and
      (iii) an integrated spectral response measurement of all or part of said shoulder minus the integrated spectral response measurement at the baseline of said curve.

28. The method of claim 27, wherein the determination of the spectral response curve in step (a) is carried out with the film being on a black substrate and/or over a black background.

* * * * *